(12) United States Patent
Edwin

(10) Patent No.: US 6,358,276 B1
(45) Date of Patent: Mar. 19, 2002

(54) FLUID CONTAINING ENDOLUMINAL STENT

(75) Inventor: Tarun J. Edwin, Tempe, AZ (US)

(73) Assignee: Impra, Inc., Tempe, AZ (US)

( * ) Notice: Subject to any disclaimer, the term of this patent is extended or adjusted under 35 U.S.C. 154(b) by 0 days.

(21) Appl. No.: 09/321,496

(22) Filed: May 27, 1999

Related U.S. Application Data
(60) Provisional application No. 60/105,768, filed on Sep. 30, 1998.

(51) Int. Cl.[7] ............................ A61F 2/06; A61M 29/00; A61M 37/00
(52) U.S. Cl. ...................... 623/1.42; 623/1.22; 606/194; 604/53; 604/500
(58) Field of Search ................................ 623/1.1, 1.11, 623/1.24, 1.25, 1.27, 1.35, 1.42, 1.22; 606/192, 194, 195; 604/96, 508, 53, 247, 246, 533

(56) References Cited

U.S. PATENT DOCUMENTS

| | | | |
|---|---|---|---|
| 3,868,956 A | 3/1975 | Alfidi et al. | |
| 4,307,723 A | 12/1981 | Finney | |
| 4,503,569 A | 3/1985 | Dotter | |
| 4,531,933 A * | 7/1985 | Norton et al. | 604/8 |
| 4,694,838 A * | 9/1987 | Wijayarthna et al. | 128/658 |
| 4,706,671 A | 11/1987 | Weinrib | |
| 4,762,130 A | 8/1988 | Fogarty et al. | |
| 4,795,458 A | 1/1989 | Regan | |
| 4,813,925 A | 3/1989 | Anderson, Jr. et al. | |
| 4,820,298 A | 4/1989 | Leveen et al. | |
| 4,881,939 A | 11/1989 | Newman | |
| 4,887,996 A * | 12/1989 | Bengmark | 604/54 |
| 4,917,666 A | 4/1990 | Solar et al. | |
| 5,147,370 A | 9/1992 | McNamara et al. | |
| 5,156,620 A | 10/1992 | Pigott | |
| 5,163,928 A * | 11/1992 | Hobbs et al. | 604/281 |
| 5,181,911 A | 1/1993 | Shturman | |
| 5,226,888 A | 7/1993 | Arney | |
| 5,370,691 A | 12/1994 | Samson | |
| 5,380,307 A * | 1/1995 | Chee et al. | 604/264 |
| 5,441,516 A | 8/1995 | Wang et al. | |
| 5,445,594 A | 8/1995 | Elist | |
| 5,536,274 A | 7/1996 | Neuss | |
| 5,545,135 A | 8/1996 | Iacob et al. | |
| 5,649,978 A | 7/1997 | Samson | |
| 5,669,931 A | 9/1997 | Kupiecki et al. | |
| 5,676,685 A | 10/1997 | Razavi | |
| 5,697,968 A | 12/1997 | Rogers et al. | |
| 5,795,318 A | 8/1998 | Wang et al. | |
| 5,882,335 A * | 3/1999 | Leone et al. | 604/96 |
| 5,902,266 A * | 5/1999 | Leone et al. | 604/53 |
| 6,050,986 A * | 4/2000 | Hektner | 604/508 |
| 6,053,900 A * | 4/2000 | Brown et al. | 604/500 |
| 6,063,101 A * | 5/2000 | Jacobsen et al. | 606/194 |

FOREIGN PATENT DOCUMENTS

WO    WO 96/26682    9/1996

* cited by examiner

Primary Examiner—David H. Willse
Assistant Examiner—A. Stewart
(74) Attorney, Agent, or Firm—Todd W. Wight; Morrison & Foerster

(57) ABSTRACT

An endoluminal stent contains a hollow passageway for the circulation of fluids to treat vascular walls affected with malignant growths or experiencing restenosis. The hollow passageway stent can have one or a plurality of passageways and is configured in a tubular shape with numerous coils, providing an empty tubular lumen through the center of the stent to allow blood flow. The stent is connected to a removable catheter that conducts fluid to the stent. Fluid flow may be regulated by valves incorporated in either the stent and/or the catheter. The stent and catheter are connected to avoid leakage of the fluid. Cryogenic, heated or radioactive fluids are circulated through the stent to treat the affected sites. A method of delivering drugs to the vascular wall is also provided by creating a stent with porous outer walls to allow diffusion of the drug.

22 Claims, 5 Drawing Sheets

FLUID CONTAINING ENDOLUMINAL STENT

CROSS-REFERENCE TO RELATED APPLICATIONS

This application claims the benefit of U.S. Provisional application No. 60/105,768, filed Sep. 30, 1998, which is incorporated fully herein by reference.

BACKGROUND OF THE INVENTION

1. Field of the Invention

The present invention relates generally to endoluminal devices, and more particularly to stents.

2. Description of Related Art

Stents and similar endoluminal devices have been used to expand a constricted vessel to maintain an open passageway through the vessel in many medical situations, for example, following angioplasty of a coronary artery. In these situations, stents are useful to prevent restenosis of the dilated vessel through proliferation of vascular tissues. Stents can also be used to reinforce collapsing structures in the respiratory system, the reproductive system, biliary ducts or any tubular body lumens. Whereas in vascular applications fatty deposits or "plaque" frequently cause the stenosis, in many other body lumens the narrowing or closing may be caused by malignant tissue.

Fluids have traditionally been used to pressurize the angioplasty balloons used to open restricted vessels. The balloons may have a variety of shapes including a coiled form. In such a device fluid is injected into the balloon to inflate the device and maintain turgidity. Shturman (U.S. Pat. No. 5,181,911) discloses a perfusion angioplasty catheter wound into a helically coiled shape with one end attached to a fitting and the other to a syringe for inflating the balloon with fluid. When the balloon is inflated, its coiled form allows blood flow thorough the open center of the structure. At the same time it is possible to actually have fluid flow within the balloon structure so that the syringe can deliver fluid into the balloon, fluid can flow through the balloon, and fluid can then exit through a second lumen in a catheter attached to the syringe.

Coiled stents that are connected to a catheter apparatus, as in Wang et al. (U.S. Pat. No. 5,795,318), are used for temporary insertion into a patient. Wang et al. discloses a coiled stent of shape-memory thermoplastic tube that can be converted from a relatively narrow diameter to a larger coiled form by heating. The narrow diameter coil is mounted at the end of a catheter over a balloon and in a preferred embodiment a resistive heating element runs down the length of the thermoplastic element. An electric current is applied to heat the element thereby softening it while the balloon is expanded to enlarge the diameter of the coil. Upon cooling the enlarged coil hardens and the balloon is withdrawn. After the temporary stent has performed its duty, it is again heated and removed while in the softened state. In one embodiment the thermoplastic tube is supplied with an additional lumen so that liquid drugs can flow into the stent and delivered through apertures or semipermeable regions.

The attempt to kill or prevent proliferation cells is a common theme in clinical practice. This is generally true in vascular and non-vascular lumens. It is known that ionizing radiation can prevent restenosis and malignant growth. Although the effect of temperature extremes, e.g., cryogenic (cold) or hot temperatures, on cellular activity is not as well researched, it may provide a safer approach to control of tissue proliferation. Among the drawbacks of the prior art coiled balloons is that the balloon material is relatively weak so that expansion and contraction cause the balloon to fail. Failure of a balloon containing radioactive or cryogenic fluids could be catastrophic. It would be desirable to provide a catheter based, minimally invasive device for stenting support that could deliver hot or cryogenic or radioactive fluids or drugs and that would be sturdy and could remain in the body for extended periods of time, detached from the insertion device.

SUMMARY OF THE INVENTION

In its simplest embodiment the present invention is an endoluminal coil stent comprising a hollow tube formed into a series of loops or other known stent shapes which initially has a low profile and diameter. This structure can be delivered into a patient's vascular system and expanded to full size. The present invention to provides a stent that is hollow allowing the passage of fluid. The stent has either one or a plurality of passageways for fluid flow. The stent is attached to a catheter via a special fitting so that when engaged with the catheter, fluid flows freely from the catheter to the stent with a possible return circuit through the catheter. When disengaged, the fitting prevents leakage from the stent permitting the stent to remain in place in a patient's vasculature.

This invention provides a way of treating vascular areas affected with malignant growths or experiencing restenosis from smooth muscle cell proliferation, etc. The stent is inserted in a small diameter configuration and after being enlarged to a larger diameter, acts as a support device for the areas of restenosis or malignant growth. In addition, the stent can treat these affected areas in a unique way by flowing radioactive, heated or cryogenic fluids through the stent.

The present invention also provides a way of delivering drugs to an affected site. A stent to accomplish this purpose can be composed of several different materials. For example, the stent can formed from a metal or other material with small pores machined or otherwise formed (e.g., with a laser). When such a stent is filed with a drug, that drug slowly disperses through the pores. Alternatively, an entire metal tube or portions of the tube could be formed e.g., from sintered metal powder thereby forming a porous structure for drug delivery. Another embodiment would alternate a metal tube (for structural stability) with dispensing segments inserted at various intervals. The segments would be perforated to allow seepage of the drug or would be otherwise formed from a porous material. Another embodiment employs an expanded polytetrafluoroethylene (PTFE) tube around a support wire or metal tube in the form of a coiled stent so that a hollow passageway is created between the metal and the PTFE. A drug is flowed into this space and slowly dispensed through the porous PTFE.

One embodiment of the hollow stent of the present invention comprises a shape memory metal such as nitinol. Shape memory metals are a group of metallic compositions that that have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. This enables the stent to be inserted into the body in a deformed, smaller state so that it assumes its "remembered" larger shape once it is exposed to a higher temperature (i.e. body temperature or heated fluid) in vivo.

Special fittings are incorporated at the ends of the hollow stent. These fittings facilitate the injection and removal of fluid and also allow the stent to be detached from the insertion device to be left in place in a patient. The hollow stent has an inlet and an outlet so that a complete fluid path can be created, and fluid can be continually circulated through the stent. In the simplest configuration the inlet and outlet are at opposite ends of the stent. However, if the stent is equipped with a plurality of lumens, two lumens can be connected at a distal end of the structure so that the outlet and inlet are both together at one end. Other arrangements can be readily envisioned by one of ordinary skill in the art.

The stent is inserted into the body while connected to a catheter in a small, deformed state. Once inside the patient's body the stent is advanced to a desired position and expanded to its larger full size. If the stent is composed of shape memory metal, for example, the stent expands from its small-deformed state to its remembered larger state due to the higher body temperature or due to the passage of "hot" fluid through the stent. Subsequently "treatment" fluid (e.g., heated, cryogenic or radioactive) is pumped through the catheter to the stent where it is circulated throughout the stent, treating the adjacent vascular walls. The catheter can either be left in place for a certain period of time or removed, leaving the fluid inside the stent. This would particularly be the case with radioactive fluid or with a porous drug delivery stent.

The stent can be removed by reattaching the catheter allowing one to chill and shrink the stent (in the case of a memory alloy). Alternatively, the device can readily be used in its tethered form to remove memory alloy stents of the present invention or of prior art design. For this purpose a device of the present invention is inserted into the vasculature to rest within the stent to be removed. Warm fluid is then circulated causing the stent to expand into contact with the memory alloy stent that is already in position. At this point cryogenic (e.g., low temperature) fluid is circulated causing the attached stent and the contacted stent to shrink so that the combination can be readily withdrawn.

DETAILED DESCRIPTION OF THE PREFERRED EMBODIMENT

Figure 1:
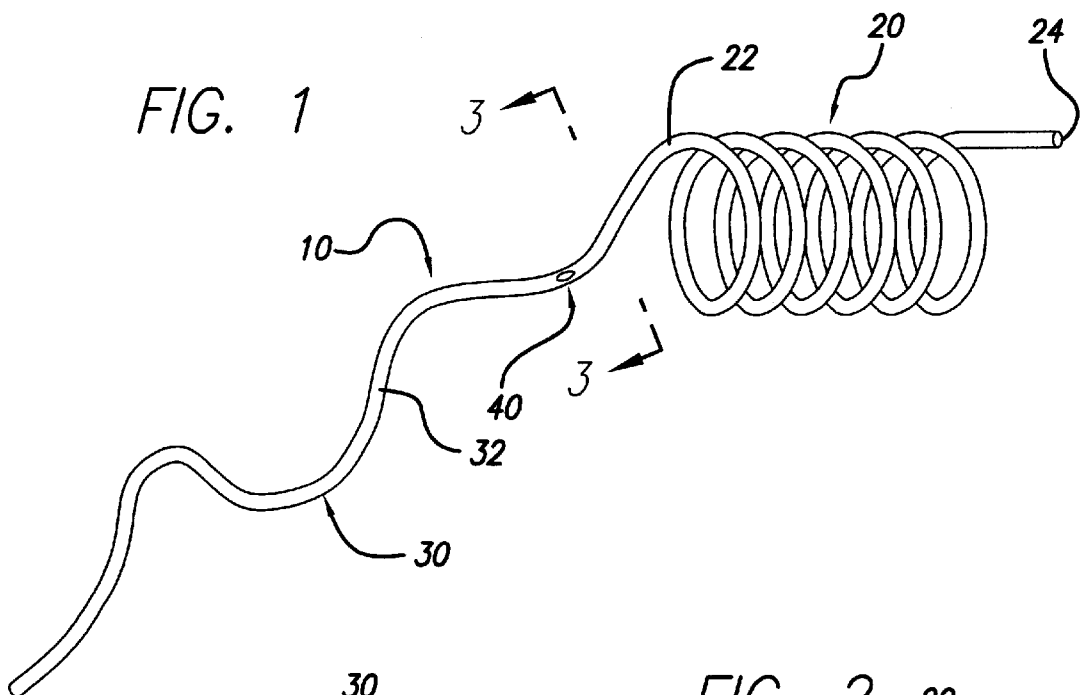
FIG. 1 is a perspective view of a hollow coiled stent.

Referring now to the drawings, in which like reference numbers represent similar or identical structures throughout the drawings, FIG.1 depicts a preferred embodiment of this invention. Pictured in FIG. 1 is a medical apparatus 10 comprising an endoluminal stent 20 attached to a delivery catheter 30 by means of a valve assembly 40. In this representation endoluminal stent 20 is generally coiled in shape leaving a tubular space down the center of its length. Obviously, the principle of a hollow stent can be applied to stents of a zigzag or other construction other than simply coiled. The tubing 22 of the stent 20 is preferably composed of a metal material that can be crimped onto a balloon catheter (not shown) for insertion into a body. Once positioned inside of the body at the desired location, the balloon can be inflated, bringing the stent from a compact small size to its enlarged full size thus opening a pathway for blood flow.

Inside the tubing 22 of stent 20, two fluid pathways exist. These pathways can be seen in the cross sectional view of FIG. 3. Pathways 26 and 28 have opposite flowing fluid streams and connect at the distal end 24 of stent 20. By allowing for opposite streams, radioactive, heated or cryogenic liquids can continuously flow through stent 20 for the purpose of killing or preventing proliferation of cells. By "heated" or "hot" is meant temperatures above body temperature. By "cryogenic" or "cold" is meant temperatures below body temperature. The stent 20 can either remain connected to a delivery catheter 30 for temporary insertion, or be detached for a more permanent insertion. In either case, fluid flow can be circulated throughout stent 20 prior to disconnection. In the simplest design, fluid passageways connected to the stent 20 are lumens of the delivery catheter so that when the catheter is withdrawn, fluid flow must cease. It is also possible to provide separate flexible tubes that are threaded through the catheter so that the delivery catheter can be withdrawn leaving the relatively smaller fluid delivery tubes (not shown) behind. Preventing leakage of the fluid from the stent 20 after the catheter 30 is disconnected is accomplished through a valve mechanism contained in the catheter 30, or the stent 20 and/or both. In the example illustrated in FIG. 2 rubber or elastomer diaphragms 25 are penetrated by small hollow needles 48 in the valve assembly 40. In addition, the valve 40 may comprise a simple back flow preventer. Thus, when pressure is applied from incoming fluid to the valve assembly 40, a ball 45 which sits in a ball seat 44 is forced back against a spring 46 and the valve 40 opens for the incoming fluid pathway 28. A similar arrangement allows pressure to open the outgoing fluid pathway 26. A check ball valve is shown only as an example. Flap valves or any of a number of other back flow valve designs well known in the art can be employed. Complex systems in which a bayonet-type attachment automatically opens a valve are also possible.

Figure 2:
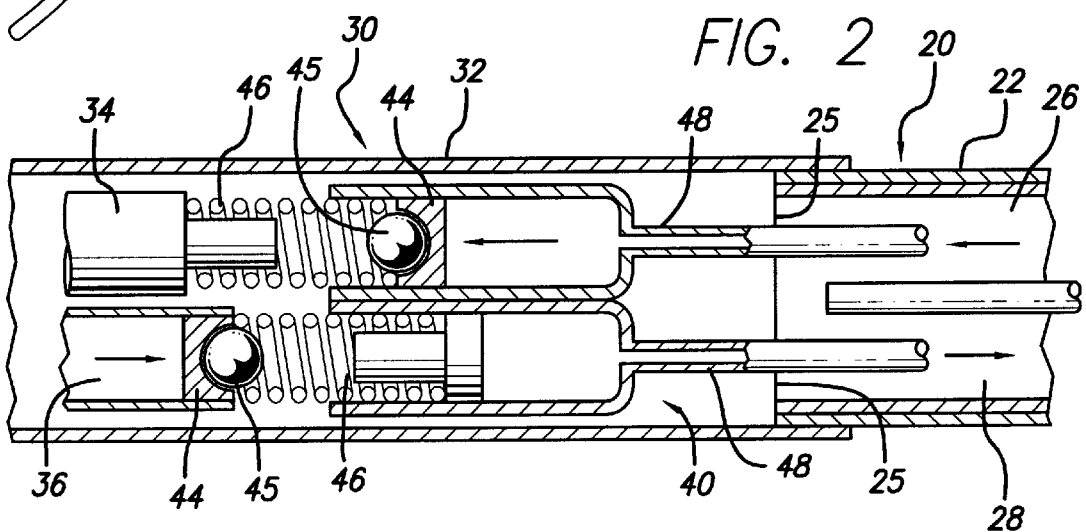
FIG. 2 is a perspective view of a valve assembly to be used with FIG. 1.
Figure 3:
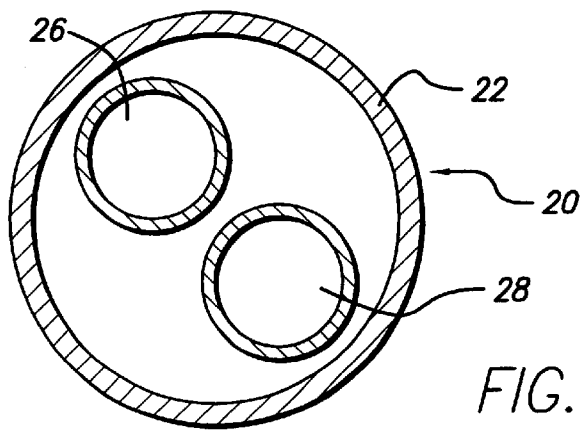
FIG. 3 is a sectional view of the hollow stent tube of FIG. 2.

The catheter 30 comprises a catheter shaft 32, which further contains two fluid pathways 34 and 36 as seen in FIG. 2. At the distal end of catheter 30, the valve assembly 40 has small hollow needles 48 that are designed to puncture elastomer diaphragms 25. The catheter 30 is slightly larger in diameter than the stent member 20 so that the catheter tubing wall 32 forms a friction fit over the stent wall 22. This creates a seal between the catheter 30 and the stent 20 for fluid delivery and removal. Upon detaching the catheter 30, leakage from the stent 20 is prevented due to the self-healing properties of the diaphragms 25. Obviously, the back flow preventer 40 could be on the stent 20 and the diaphragms could be on the catheter 30.

Figure 4:
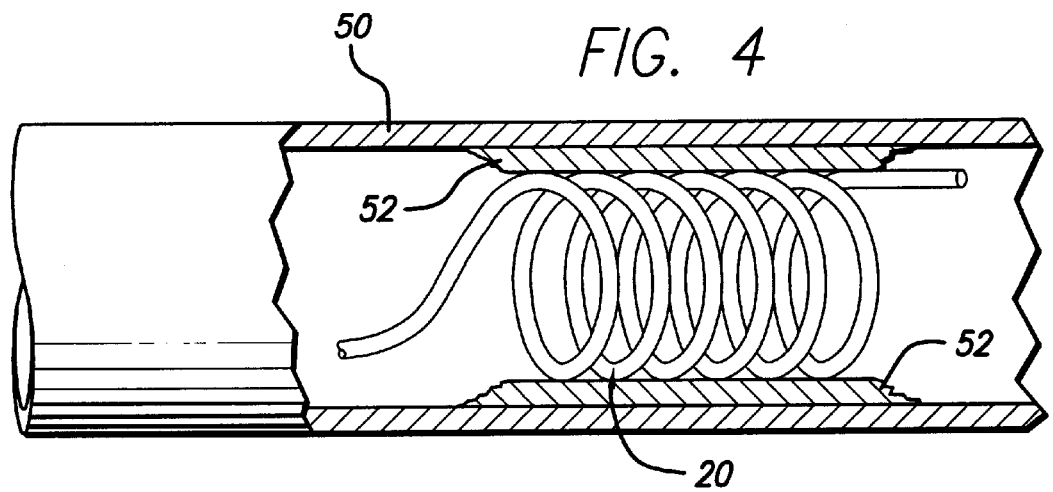
FIG. 4 is a representation of the stent of FIG. 1 in the position for treatment.

As discussed above, stent 20 is inserted into the body to the desired site through the use of a catheter insertion device well known in the art. FIG. 4 depicts stent 20 in its enlarged form after it has been inserted into the body at the affected location and expanded. Other means of stent expansion other than a balloon catheter are possible. If the stent 20 is formed from shape memory metal, such as nitinol, the heat of the body can cause the stent 20 to assume a larger, remembered form. Alternatively, heated fluid can be circulated through the stent to cause it to recover its remembered form. A self-expanding stent made of a spring-type alloy can also be employed. In that case the delivery catheter would be equipped with means (e.g., an outer sheath) to keep the stent compressed until it was at the desired location.

By increasing the diameter of stent 20 at an affected location, the passageway is enlarged to permit increased blood flow. At the same time, fluids can pass through the interior of tubes 22 of the hollow stent 20 to treat the vascular wall. The walls of the vasculature can be treated by running either a radioactive, cryogenic or heated fluid through the stent 20 or by delivering a drug through a stent equipped for drug diffusion (e.g., through holes or a porous region).

Figure 5:
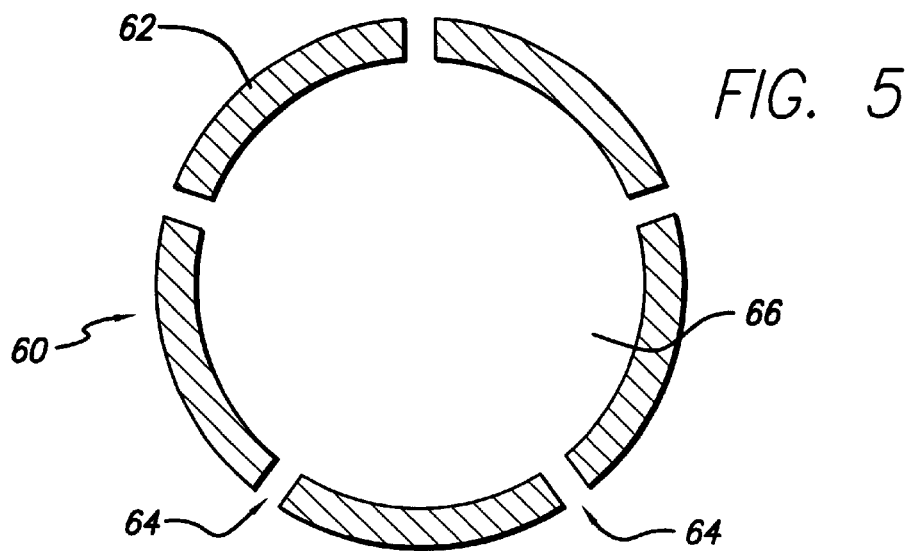
FIG. 5 is a sectional view of a second embodiment of a hollow coiled stent.
Figure 6:
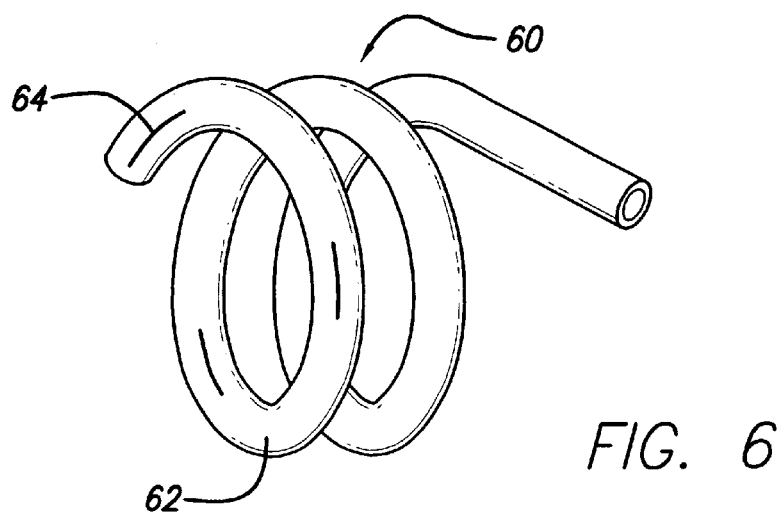
FIG. 6 is a perspective view of a second embodiment of a hollow coiled stent.

FIG. 5 depicts a second embodiment of the invention. In this embodiment, the hollow stent 60 has only one fluid pathway 66, an inlet without an outlet, and is used to deliver drugs to affected areas. Once the stent 60 is inserted into place and is in its enlarged configuration, drugs are delivered through the catheter to the stent 60. Stent 60 can be constructed in various ways to facilitate the delivery of drugs. In one case, as shown in FIG. 6, the stent 60 is constructed with regions or segments that have pores 64 to allow drug seepage from the tubing 62. Alternatively, continuously porous metal, porous plastic, or a combination of metal and plastic can be used. The perforations 64 or slits in the stent to facilitate drug delivery must be of sufficiently small size to allow the passage of the drug through the entire length of the stent so that all areas can be treated. It will be apparent that pore size can control the rate at which the drug is dispensed. It is possible to cover the pores 64 with semipermeable membrane to further control and restrict drug outflow. A semipermeable membrane with inclusion of an osmotic agent with the drug will result in water uptake and more rapid and controlled pressurized delivery of the drug.

Figure 7:
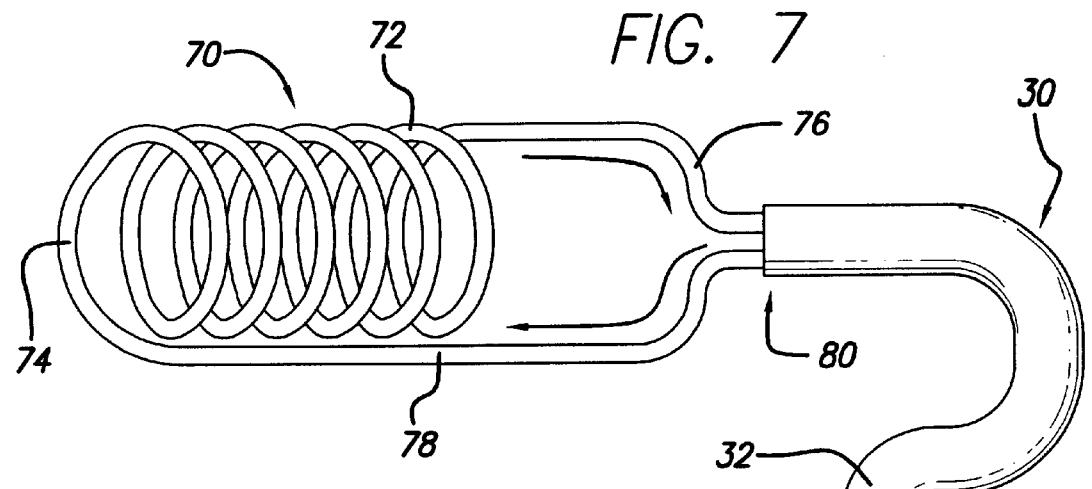
FIG. 7 is a perspective view of a third embodiment of a hollow coiled stent.
Figure 8:
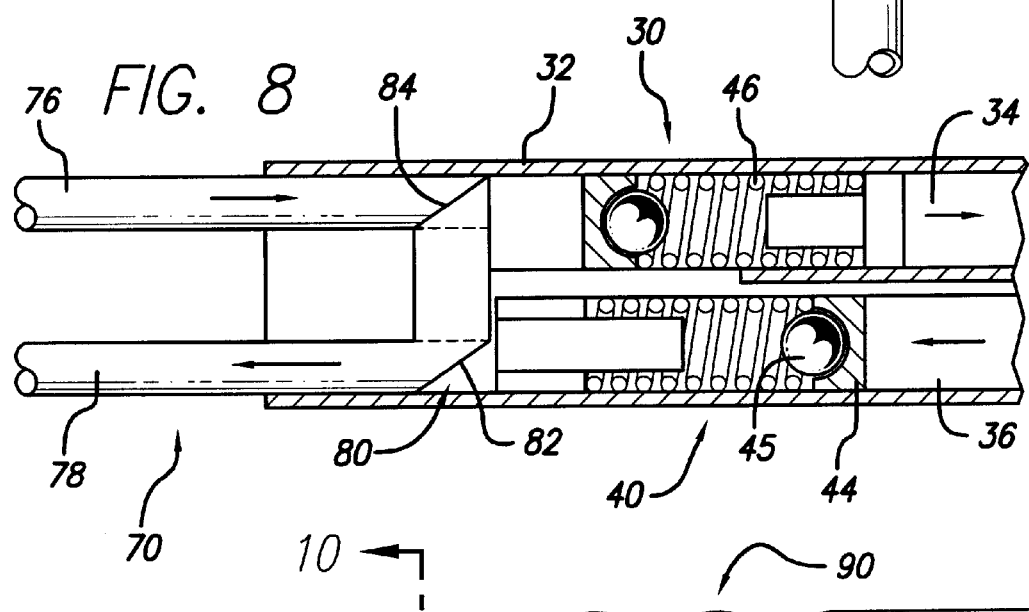
FIG. 8 is a perspective view of a valve assembly to be used with FIG. 6.

A third embodiment of the invention, FIG. 7, has a hollow stent 70 containing a single fluid pathway. The tubing 72 can be made of any of the materials discussed above, but in this embodiment, the stent 70 has an inlet path 78 that carries the fluid to the distal end 74 of stent 70 where it then runs through the coils. In this embodiment, a valve 80 connects the stent 70 to catheter 30. FIG. 8 shows a cross-sectional view of valve 80. The pressure from the liquid sent through the catheter causes the gate 82 of valve 80 to open to allow the fluid into the inlet path 78. The pressure that forces the opening of gate 82 causes the simultaneous opening of gate 84, allowing the fluid that is circulated through the stent 70 to exit through pathway 36 of catheter 30. The fluid entering and exiting through catheter 30 must also go through a check ball valve assembly similar to the one shown in FIG. 2. Again, flaps or other "one way" valve mechanisms can be applied. After all incoming fluid has been delivered to the stent 70, the absence of pressure causes gate 82 and gate 84 to close, thereby closing valve 80. This design can be used with any of the fluids mentioned above. The stent 70 can be used to circulate radioactive or cryogenic fluids for treatment of the vascular walls and can also be perforated for the delivery of drugs.

Figure 9:
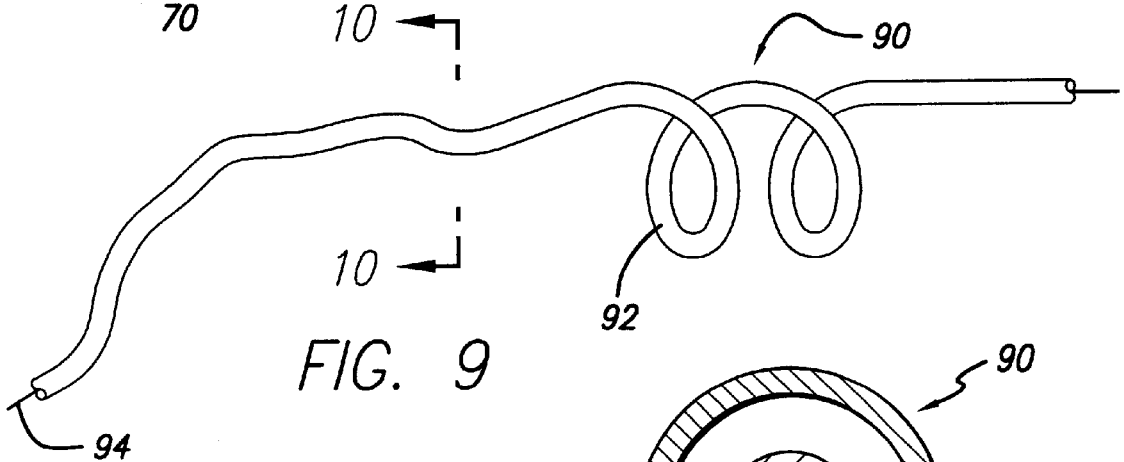
FIG. 9 is a perspective view of a fourth embodiment of a hollow coiled stent.
Figure 10:
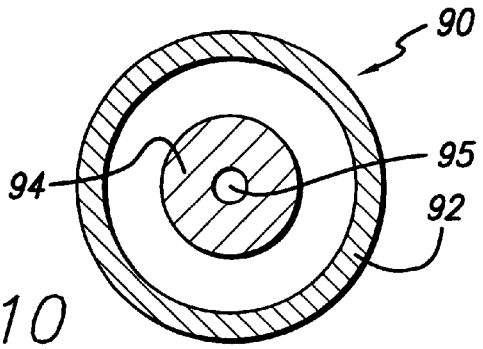
FIG. 10 is a sectional view of the hollow stent tube of FIG. 8.

In a fourth embodiment, a hollow coiled stent 90 is formed from polytetrafluoroethylene (PTFE) 92. In FIG. 9, a perspective view of this embodiment can be seen. The stent 90 consists of a support wire 94 over which PTFE 92 is fitted. The pliable structure resulting is then formed into a coiled stent. The PTFE 92 is fitted around the wire 94 so that there is sufficient room to allow the passage of fluid. FIG. 10 shows a cross-sectional view of stent 90, illustrating the pathway 96 created around the support wire 94 to allow the passage of fluid. In this embodiment, stretched expanded PTFE can be used to create a porous stent to facilitate the delivery of drugs. The wire 94 can also be hollow (passageway 95) so that the stent 90 can simultaneously deliver drugs and radioactive fluid or temperature regulating fluid.

Figure 11A:
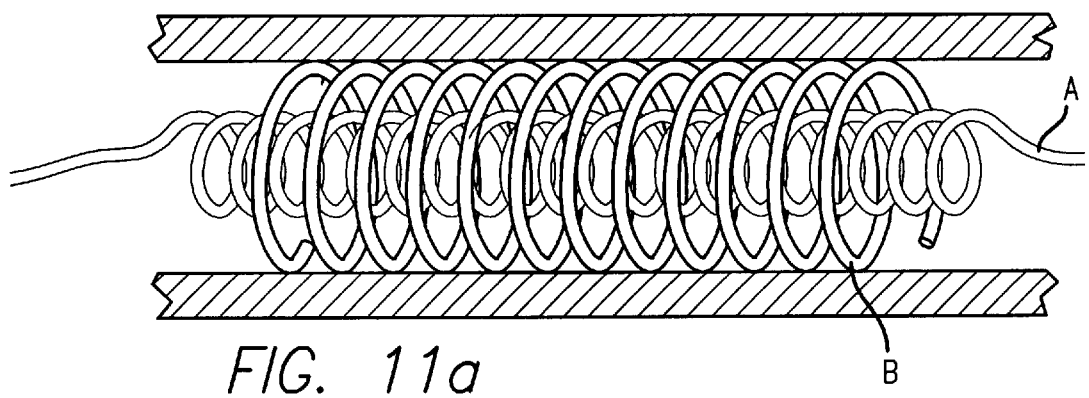
FIG. 11 (11a, 11b, and 11c) is an illustration of the method detailed in FIG. 12.
Figure 11B:
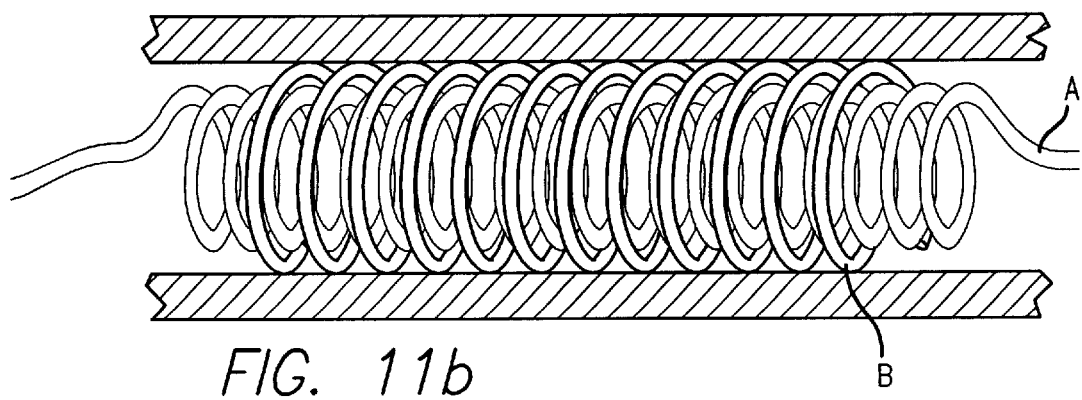
Figure 11C:
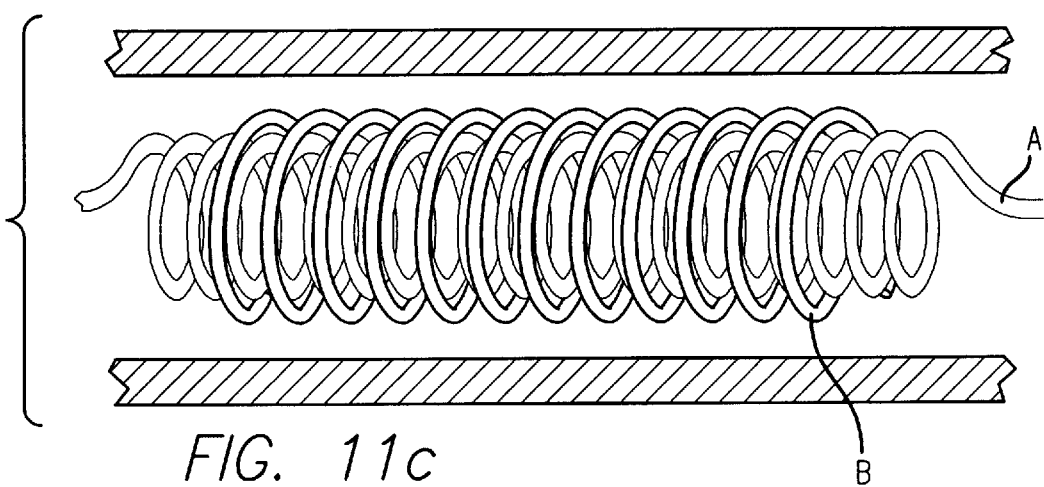
Figure 12:
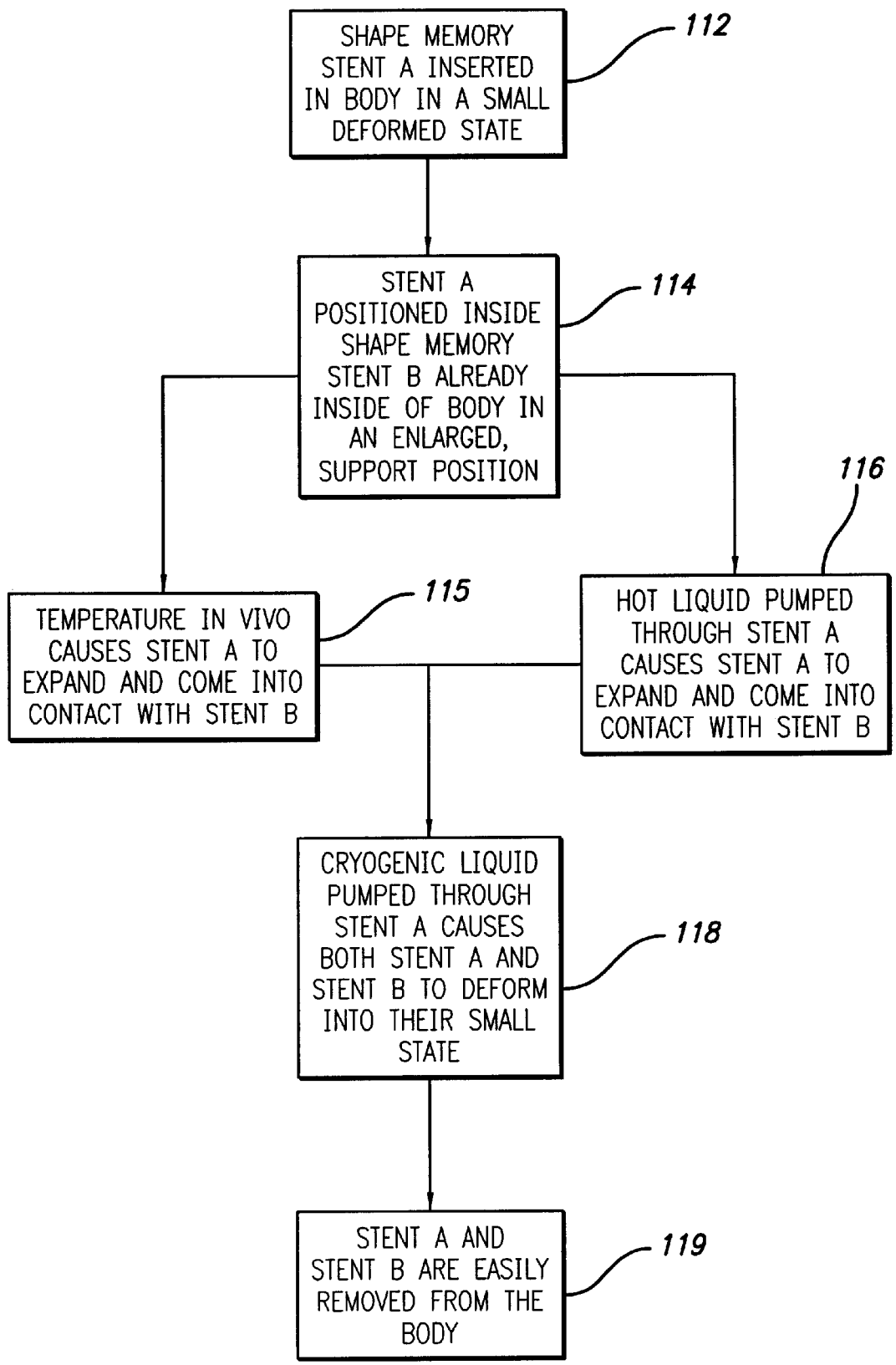
FIG. 12 is a flow diagram explaining use a stent of the present invention to retrieve a shape memory stent already in place.

A fifth embodiment of the invention is illustrated in FIG. 11 and described in a flow diagram shown in FIG. 12. This embodiment is a method for recapturing an existing shape memory metal stent already in the body. With reference to both FIGS. 11 and 12, a shape memory metal stent A is inserted into the body in its small, deformed state through the use of an insertion device well known in the art in step 112. The inserted stent A in its deformed state is placed into the center of a memory alloy stent B that is already in an enlarged support position in the body in step 114. The deformed stent A is then enlarged so that it comes in contact with stent B. This can be accomplished in one of two ways. Either the stent A may enlarge due to the higher in vivo body temperature in step 115, or a hot liquid may be pumped through stent A to cause it to expand in step 116. Once expanded and in contact with stent B, cryogenic liquid may be pumped through stent A so that both stent A and stent B are chilled and either shrink down to their deformed states or become sufficiently relaxed to allow ready removal in step 118. Once in a small, deformed or relaxed state, stents A and B are easily removed from the body in step 119 by withdrawing the catheter attached to stent A. FIG. 11a illustrates stent A in its reduced state being inserted into stent A. FIG. 11b shows an enlarged version of stent A contacting stent B. Thereafter, a temperature change caused, for example, by fluid circulating through stent A will shrink both stents and enable their removal (FIG. 11c).

Having thus described a preferred embodiment of a hollow endoluminal stent, it should be apparent to those skilled in the art that certain advantages of the within system have been achieved. It should also be appreciated that various modifications, adaptations, and alternative embodiments thereof may be made within the scope and spirit of the present invention. For example, a hollow stent with a coiled, tubular shape has been illustrated, however, many other possibilities exist for the shape and size of the hollow stent. In addition, the passageways are illustrated as round but could take on a variety of other shapes. The described embodiments are to be considered illustrative rather than restrictive. The invention is further defined by the following claims.

I claim:

1. An endoluminal stent system comprising:
   a stent comprised of non-inflatable non-porous tubing, having at least one fluid flow conduit therein, wherein the tubing is circumferentially arranged so as to form a side wall of the stent, thereby creating a main lumen of the stent through which blood can flow;
   a removable catheter wherein a proximal end remains outside of a body and a distal end is sealingly attached to the stent, wherein the catheter is adapted to deliver fluid to the stent;

connector means for attaching the removable catheter to the stent; and valve means within the system for controlling fluid flow.

2. The endoluminal stent system as described in claim 1, wherein the stent is formed from metal.

3. The endoluminal stent system as described in claim 2, wherein the stent has shape memory properties.

4. The endoluminal stent system as described in claim 1, wherein the stent is formed from plastic.

5. The endoluminal stent system as described in claim 1, further comprising a core that is positioned within, but spaced apart from, an outer wall of the tubing, creating an annular region therebetween.

6. The endoluminal stent device as described in claim 5, wherein said core contains a hollow passageway.

7. The endoluminal stent system as described in claim 1, wherein the tubing is formed into a coiled structure.

8. The endoluminal stent system as described in claim 1, wherein the tubing has a circular shape in cross-section.

9. An endoluminal stent device comprising:

a stent defined by a non-inflatable non-porous outer wall adapted to accommodate a fluid therein, wherein the outer wall is arranged into a coiled structure so as to form a side wall of the stent, thereby creating a main lumen of the stent through which blood can flow;

a removable catheter wherein a proximal end remains outside of a body and a distal end is sealingly attached to a connector, wherein the catheter is adapted to deliver fluid to the stent; and valve means within the device for controlling fluid flow.

10. The endoluminal stent device as described in claim 9, wherein said valve means are contained within said stent.

11. The endoluminal stent device as described in claim 9, wherein said valve means are contained within said catheter.

12. The endoluminal stent device as described in claim 9, wherein the stent is formed from metal.

13. The endoluminal stent device as described in claim 12, wherein the stent has shape memory properties.

14. The endoluminal stent device as described in claim 9, wherein the stent is formed from plastic.

15. The endoluminal stent device as described in Claim 9, further comprising a core that is positioned within, but spaced apart from, the outer wall of the stent, creating an annular region therebetween.

16. The endoluminal stent device as described in claim 15, wherein said core contains a hollow passageway.

17. The endoluminal stent device as described in claim 9, wherein the outer wall has a circular shape in cross-section.

18. An endoluminal stent apparatus comprising:

a stent comprised of a support wire surrounded by an expanded polytetrafluoroethylene tubing, creating a first lumen therebetween, wherein the combination of support wire and expanded polytetrafluoroethylene tubing is arranged into a coiled structure so as to form a side wall of the stent, thereby creating a main lumen of the stent through which blood can flow, wherein the tubing includes a plurality of porous segments spaced apart from each other along a length thereof, and wherein the support wire is hollow, creating a second lumen coaxial with the first lumen; and a removable catheter, wherein a proximal end remains outside of a body and a distal end is sealingly attached to the stent, wherein the catheter is adapted to deliver fluid to the stent.

19. The endoluminal stent apparatus as described in claim 18, further comprising connector means for attaching the removable catheter to the stent.

20. The endoluminal stent apparatus as described in claim 18, further comprising valve means for controlling fluid flow in the system.

21. The endoluminal stent system as described in claim 1, further comprising two fluid flow conduits, wherein said conduits are distinct and separate at a proximal end of the stent, and wherein said conduits are connected at a distal end of the stent.

22. The endoluminal stent device as described in claim 9, further comprising two fluid conduits, wherein said conduits are distinct and separate at a proximal end of the stent, and wherein said conduits are connected at a distal end of the stent.

* * * * *